US008969417B2

(12) United States Patent
Lamensdorf et al.

(10) Patent No.: US 8,969,417 B2
(45) Date of Patent: Mar. 3, 2015

(54) PHARMACEUTICAL COMPOSITIONS FOR TREATMENT OF PARKINSONS DISEASE

(75) Inventors: Itschak Lamensdorf, Modiin (IL); Yoram Sela, Raanana (IL)

(73) Assignee: Pharmatwob Ltd., Rehovot (IL)

(*) Notice: Subject to any disclaimer, the term of this patent is extended or adjusted under 35 U.S.C. 154(b) by 514 days.

(21) Appl. No.: 12/996,455

(22) PCT Filed: Jun. 7, 2009

(86) PCT No.: PCT/IL2009/000567
§ 371 (c)(1),
(2), (4) Date: Jun. 7, 2011

(87) PCT Pub. No.: WO2009/147681
PCT Pub. Date: Dec. 10, 2009

(65) Prior Publication Data
US 2011/0230513 A1    Sep. 22, 2011

Related U.S. Application Data

(60) Provisional application No. 61/059,326, filed on Jun. 6, 2008.

(51) Int. Cl.
| | | |
|---|---|---|
| *A61K 31/135* | (2006.01) | |
| *A61K 31/428* | (2006.01) | |
| *A61K 45/06* | (2006.01) | |
| *A61K 31/137* | (2006.01) | |
| *A61K 31/4045* | (2006.01) | |

(52) U.S. Cl.
CPC .............. *A61K 45/06* (2013.01); *A61K 31/135* (2013.01); *A61K 31/137* (2013.01); *A61K 31/4045* (2013.01); *A61K 31/428* (2013.01)
USPC .......................................... 514/650; 514/366

(58) Field of Classification Search
None
See application file for complete search history.

(56) References Cited

U.S. PATENT DOCUMENTS

| 4,812,481 | A | 3/1989 | Reischig et al. |
|---|---|---|---|
| 5,221,536 | A | 6/1993 | Edgren et al. |
| 2006/0204449 | A1 | 9/2006 | Rolland et al. |
| 2007/0225379 | A1 | 9/2007 | Carrara et al. |

FOREIGN PATENT DOCUMENTS

| WO | 91/16885 A | 11/1991 |
|---|---|---|
| WO | 01/78711 A2 | 10/2001 |
| WO | 2004/089353 A2 | 10/2004 |
| WO | WO 2004089353 A2 * | 10/2004 |
| WO | 2007/002518 A1 | 1/2007 |
| WO | 2007/048034 A2 | 4/2007 |
| WO | 2007/073702 A | 7/2007 |
| WO | 2007/093450 A2 | 8/2007 |
| WO | 2007/117431 A2 | 10/2007 |
| WO | 2007/137071 A2 | 11/2007 |
| WO | 2008/008398 A2 | 1/2008 |
| WO | 2008/013860 A2 | 1/2008 |
| WO | 2008/021368 A2 | 2/2008 |
| WO | 2008/024371 A2 | 2/2008 |
| WO | 2008/041140 A2 | 4/2008 |
| WO | 2008/053352 A2 | 5/2008 |
| WO | WO 2008129043 A1 * | 10/2008 |

OTHER PUBLICATIONS

Seeberger et al., Optimizing bioavailability in the treatment of Parkinson's disease, Neuropharmacology 53 (2007) 791-800.*
Rinne, Combination of a dopamine agonist, MAO-B inhibitor and levodopa—a new strategy in the treatment of early Parkinson's . disease, Acta Neurol. Scand., 1989; 126: 165-169.*
Martignoni et al., Lisuride plus selegiline in the treatment of early Parkinson's disease, Acta Neurol. Scand., 1991; 83(6): 407-410.*
Chen Shengdi et al., Parkinson Disease, People's Medical Publishing House, pp. 329-335. (2006), Reviewed assuming the reference is Chapter 28 Therapy of Parkinson's disease with Type B Monoamine Oxidase Inhibitor.
Rinne U.K., "Combination of a dopamine agonist, MAO-B inhibitor and levodopa—a new strategy in the treatment of early Parkinson's disease", Acta Neurologica Scandinavica, 126, pp. 165-169 (1989).
Nappi et al. "Lisuride plus selegiline in the treatment of early Parkinson's disease", Acta Neurologica Scandinavica, 83(6), pp. 407-410 (1991).
Rascal et al., Rasagiline as an adjunct to levodopa in patients with Parkinson's disease and motor fluctuations (LARGO, Lasting effect in Adjunct therapy with Rasagiline Given Once daily, study): a randomized, double-blind, parallel-group trial. Lancet, vol. 365, pp. 947-954. (2005).
Hubble et al., "Pramipexole in patients with early Parkinson's disease" Clin. Neuropharmacol, vol. 18, No. 4, pp. 338-347 (1995).
Dechant et al., "Ropinirole" CNS Drugs, vol. 8, No. 4 pp. 335-341 (1997).

(Continued)

*Primary Examiner* — Svetlana M Ivanova
(74) *Attorney, Agent, or Firm* — Browdy and Neimark, PLLC (57) ABSTRACT

Pharmaceutical compositions are provided for treatment of Parkinson's disease comprising a pharmaceutically acceptable carrier and a fixed dose combination of two active agents selected from compounds having either neuroprotective or symptomatic effects, or both, in Parkinson's disease patients, wherein the molar ratio of the two compounds is in the range of 1:1 to 1:100. The compositions are formulated for immediate release, controlled release, or both immediate and controlled release.

5 Claims, 6 Drawing Sheets

(56) References Cited

OTHER PUBLICATIONS

"A Non-Blinded Study Demonstrating the Effectiveness and Safety of Azilect Alone or in Combination Therapy in Parkinson's Disease" www.clinicaltrials.gov—Internet Citation, [Online] Nov. 10, 2006.
Wilson et al.,"LEGATO: Early rapid clinical benefit with Azilect (R) (rasagiline tablets) as mono- and adjunct therapy on Parkinson's disease (PO) symptoms—A multicenter phase IV trial" Neurology, vol. 70, No. 11, Suppl. 1, p. A60, (2008).
Seeberger et al.: "Optimizing bioavailability in the treatment of Parkinson's disease" Neuropharmacology, vol. 53, No. 7, pp. 791-800 (2007).
"Overview of Parkinson's Disease" Journal of The American Medical Directions Association, Elsevier, NL., vol. 6, No. 4, 1 pp. 4-16 (2005).
King et al. "Case series: amantadine open-label treatment of impulsive and aggressive behavior in hospitalized children with developmental disabilities." Journal of The American Academy of Child and Adolescent Psychiatry vol. 40, No. 6, pp. 654-657 (2001).
Teva Neuroscience, Inc., FDA Approved Labeling Text for NDA 021641/S-002/2-003/S-004/S-005/S-007/S-008/S-010, dated Dec. 9, 2009, pp. 1-5.
The Parkinson Study Group PramiBID Investigators, (Kieburtz, et al.), Twice-Daily, Low-Dose Pramipexole in Early Parkinson's Disease: A Randomized, Placebo-Controlled Trial, Movement Disorders, 2011, pp. 37-44, vol. 26, No. 1.
Newron Pharmaceuticals, Press Release, Safinamide Phase III MOTION and SETTLE study results presented at 2013 American Academy of Neurology (AAN) Annual Meeting, Mar. 19, 2013, pp. 1-5.
Nyholm, D., Abstract Only, Pharmacokinetic optimisation in the treatment of Parkinson's disease: an update, Clin. Pharmacokinet, 2006, pp. 109-136, vol. 45(2), Pubmed ID 16485914.
Anonymous, Abstract Only, Safinamide is a Ca and Na Channel Antagonist, Drugs R D, 2004, pp. 355-358, vol. 5 (6), Pubmed ID 15563241.

* cited by examiner

PHARMACEUTICAL COMPOSITIONS FOR TREATMENT OF PARKINSONS DISEASE

TECHNICAL FIELD

The present invention is in the field of neurodegenerative diseases and, in particular, relates to compositions and methods for treatment of Parkinson's disease.

BACKGROUND ART

Parkinson's disease is a neurodegenerative disorder characterized by a chronic and progressive loss of dopamine neurons in substantia nigra pars compacta, leading to movement disorders including dyskinesia, resting tremor, rigidity, and gait disturbance.

The medical treatment of Parkinson's disease is directed to stopping, slowing down, reducing the extent of or minimizing the neurodegenerative process in nigrostriatal neurons (neuroprotective therapy) and eliminating the biochemical imbalance (symptomatic therapy). The main directions of symptomatic therapy in Parkinson's disease are to increase dopamine synthesis, or stimulate dopamine receptors activity and dopamine release from the presynaptic space, and to inhibit dopamine reuptake by presynaptic receptors and dopamine catabolism.

The gold standard in the pharmacological treatment of Parkinson's disease is provided by DOPA-containing substances such as levodopa. Levodopa is commonly administered in combination with carbidopa, which increases the half-life of levodopa. However, the efficacy of these agents decreases over time because of continuing degeneration of neurons in the substantia nigra.

SUMMARY OF THE INVENTION

The present invention provides formulations comprising known drugs used or proposed for the treatment of Parkinson's disease formulated in a way that such drugs will be more effective for improving the patient's conditions.

In one aspect, the present invention relates to pharmaceutical compositions for treatment of Parkinson's disease comprising a fixed dose combination of two different active agents selected from compounds having a symptomatic or neuroprotective effects, or both, in Parkinson's patients, wherein the molar ratio of the two compounds is in the range of 1:1 to 1:100.

In another aspect, the present invention provides a method for treatment of Parkinson's disease, comprising administering to a patient in need a pharmaceutical composition comprising the drug combinations of the invention.

BRIEF DESCRIPTION OF DRAWINGS

FIGS. 1 A-C show neuroprotective effect of Parkinson drugs and combinations of the drugs on serum-free medium induced apoptosis in PC12 cells as measured by % viable cells. FIG. 1A: (1) Starvation; (2) ropinirole, 200 µM; (3) ropinirole, 100 µM; (4) rasagiline, 50 µM; (5) rasagiline, 100 µM; (6) combination of ropinirole, 200 µM:rasagiline, 50 µM; (7) combination of ropinirole, 100 µM:rasagiline, 10 µM; FIG. 1B: (1) Starvation; (2) pramipexole, 200 µM; (3) pramipexole, 100 µM; (4) selegiline, 50 µM; (5) selegiline, 10 µM; (6) combination of pramipexole, 50 µM; (7) combination of pramipexole, 100 µM:selegiline, 10 µM; FIG. 1C: (1) starvation; (2) ropinirole, 200 µM; (3) ropinirole, 100 µM; (4) selegiline, 50 µM; (5) selegiline, 10 µM; (6) combination of ropinirole, 200 µM:selegiline, 50 µM; (7) combination of ropinirole, 100 µM:selegiline, 10 µM.

FIGS. 2 A-D show neuroprotective effect of Parkinson drugs and combinations on MPP+ induced apoptosis in PC12 cells as measured by % viable cells. In FIGS. 2A-C the neuroprotective effect is measured as % viability of control, while in FIG. 2D it is measured as % toxicity. FIG. 2A: (1) MPP+, 250 µM; (2) ropinirole, 400 µM; (3) ropinirole, 200 µM; (4) ropinirole, 100 µM; (5) rasagiline, 100 µM; (6) rasagiline, 50 µM; (7) rasagiline, 10 µM; (8) combination of ropinirole, 400 µM:rasagiline, 100 µM; (9) combination of ropinirole, 200 µM:rasagiline, 50 µM; (10) combination of ropinirole, 100 µM:rasagiline, 10 µM; FIG. 2B: (1) MPP+, 250 µM; (2) ropinirole, 400 µM; (3) ropinirole, 200 µM; (4) selegiline, 100 µM; (5) selegiline, 50 µM; (6) combination of ropinirole, 400 µM:selegiline, 100 µM; (7) combination of ropinirole, 200 µM:selegiline, 50 µM; FIG. 2C: (1) MPP+, 250 µM; (2) pramipexole, 400 µM; (3) rasagiline, 100 µM; (4) selegiline, 100 µM; (5) combination of pramipexole, 400 µM:rasagiline, 100 µM; (6) combination of pramipexole, 400 µM:selegiline, 100 µM. FIG. 2D: (1) MPP+, 500 µM; (2) pramipexole, 400 µM; (3) rasagiline. 400 µM; (4) combination of pramipexole, 200 µM:rasagiline, 200 µM; (5) Control.

DETAILED DESCRIPTION OF THE INVENTION

In one aspect, the present invention relates to combination treatment of Parkinson's disease patients with two different active agents.

A combination treatment with two agents that act through two different mechanisms of action, for example one with a neuroprotective effect, and the other inducing symptomatic effect by increasing dopamine synthesis in the brain, has a very good chance of synergistic beneficial therapeutic value. Also agents with anti-apoptosis activity or anti-oxidative stress activity may be beneficial in combination with anti-cholinesterase inhibitors or NMDA antagonists.

The rational behind this aspect of the present invention is that the ratio of the two combination components must be precisely calibrated and that the two components are preferably formulated in a single dosage form designed for optimal pharmacokinetic performance and efficacy and for patient's compliance. The term "Fixed Dosage Combination" is used herein to describe a single dosage formulation comprising two different drugs at a precise ratio, namely, in certain fixed doses. For a treatment based on multiple drugs the exact ratio of the components, timing, dosing and pharmacokinetic aspects play an extremely important role. To determine the optimal Fixed Dosage Combination, not only the combined/synergistic efficacy and potency are of importance, but also the relative pharmacokinetics of each component and the optimal formulation.

The superior therapeutic effect of the combinations of the present invention over current monotherapies and combination therapies for Parkinson's disease is due to the unique ratio and formulations that provide optimal pharmacokinetic properties and improves either one or both agents' absorption, half life and distribution.

Thus, according to this aspect, the invention provides a pharmaceutical composition for treatment of Parkinson's disease comprising a pharmaceutically acceptable carrier and two active agents selected from compounds having either neuroprotective or symptomatic effects, or both, in Parkinson's disease patients, wherein the molar ratio of the two compounds is in the range of 1:1 to 1:100.

The compound having either neuroprotective or symptomatic effects, or both, may be selected from two different groups of the following agents: (i) a dopamine receptor agonist (DRA); (ii) a monoamine oxidase (MAO) inhibitor; (iii) levodopa alone, or in combination with a decarboxylase inhibitor and/or a catechol-O-methyl transferase (COMT) inhibitor; (iv) a glutamate receptor agonist or antagonist; (v) a spin-trapping agent; (vi) an anti-oxidant agent; or (vii) an anti-inflammatory agent.

In one embodiment, one of the active agents is a dopamine receptor agonist (DRA) able to stimulate dopamine receptors in nerves in the brain that normally would be stimulated by dopamine. The agonist may have a selective action on dopamine receptor subtypes. Examples of dopamine receptor agonists that may be used according to the invention include, but are not limited to, pramipexole, ropinirole piribedil, lisuride, cabergoline, apomorphine, rotigotine, bromocriptine and pergolide.

In preferred embodiments, the agonist is pramipexole, ropinirole and apomorphine, most preferably pramipexole and ropinirole. Pramipexole and apomorphine have both symptomatic and neuroprotective effects, and ropinirole has symptomatic effect.

In a further embodiment, one of the two active agents is a MAO inhibitor, preferably a propargylamine type MAO-B inhibitor such as rasagiline and selegiline, both approved drugs for treatment of Parkinson's disease.

The principal rationale for MAO inhibition in Parkinson's disease is enhancement of striatal dopamine activity, which results in symptomatic motor benefits. MAO inhibitors also increase the level of dopamine by inhibiting the monoamine oxidase B, the enzyme responsible for its hydrolysis. In addition, due to their antioxidant and antiapoptotic activities, MAO-B inhibitors also exhibit neuroprotective activity.

In still a further embodiment, one of the active agent is levodopa (L-DOPA), a precursor of dopamine, which is able to cross the blood-brain barrier, while dopamine itself cannot. In the central nervous system, levodopa is metabolized to dopamine by aromatic L-amino acid decarboxylase (herein "decarboxylase") and increases dopamine levels in the brain, being therefore indicated for symptomatic treatment of Parkinson's disease. However, levodopa is also converted to dopamine in the peripheral tissues, i.e. outside the brain. In order to prevent peripheral formation of dopamine, in one embodiment a peripheral decarboxylase inhibitor such as carbidopa or benserazide is coadministered with levodopa. In another embodiment, a catechol-O-methyl transferase (COMT) inhibitor such as tolcapone or entacapone is coadministered along with levodopa and carbidopa to prevent synthesis of dopamine in peripheral tissue. Since both carbidopa and the COMT inhibitors themselves have no beneficial effect when given alone to Parkinson's disease patients, they are not considered as active agents according to the present invention.

In yet another embodiment, one of the two active agents is a glutamate receptor agonist or antagonist such as, but not limited to, amantadine, minocycline and remacemide.

The glutaminergic subthalamopallidal pathway is hyperactive after dopamine depletion leading to excessive transmission from the subthalamic nucleus and subthalamopallidal glutaminergic pathways that results in akinesia and rigidity. Inhibition of these pathways by glutamate receptor antagonists restores the balance of acetylcholine and dopamine transmission and reverses these motor symptoms. It is hypothesized that the pathogenesis of Parkinson's disease may be mediated by glutamate-induced neuronal injury and that glutamate antagonists may be neuroprotective in Parkinson's disease.

The abnormal functioning of synaptic excitatory amino acid neurotransmitter (principally glutamate and aspartate) and other central excitatory and inhibitory neurotransmitters play a role in the development and progression of a range of neurodegenerative brain disorders, including epilepsy, Parkinson's disease and Alzheimer's disease. These include N-methyl d-aspartate (NMDA)- and non-NMDA sub-type glutamate receptor antagonists and metabotropic glutamate receptor agonists and antagonists, acting pre- and/or post functionally at the central excitatory synapse. Antagonists of Group I and agonists of Group II and III mGlu receptors exhibit neuroprotective and symptom-ameliorating properties.

Since NMDA receptors are one of the most harmful factors in excitotoxicity, antagonists of the receptors have held much promise for the treatment of conditions that involve excitotoxicity, including traumatic brain injury, stroke, and neurodegenerative diseases such as Alzheimer's, Parkinson's, and Huntington's.

In one embodiment, one of the active agents is an NMDA receptor antagonist. Amantadine is an NMDA receptor antagonist and an anticholinergic drug and has both symptomatic and neuroprotective effects. Minocycline, a member of the broad spectrum tetracycline antibiotics, has neuroprotective properties. Both minocycline, a member of the broad spectrum tetracycline antibiotics, and remacemide have neuroprotective properties.

In still another embodiment, one of the two active agents is a spin-trapping agent such as, but not limited to, 4-hydroxy-[2,2,6,6-tetramethylpiperidine-1-oxyl (tempol), α-(4-pyridyl-1-oxide)-N-tert-butyl nitrone (POBN), or α-phenyl-tert-butyl nitrone (PBN), known as neuroprotective agents.

In yet another embodiment, one of the two active agents is an antioxidant showing neuroprotective effect such as, but not limited to, melatonin; vitamin C; vitamin D; β-carotene; estrogens such as 17β-estradiol; phenolic compounds such as vitamin E, 2,4,6-trimethylphenol, N-acetylserotonin, and 5-hydroxyindole; and cannabinoids. Among the family of steroidal molecules, only estrogens have the capability of preventing neuronal cell death caused by increased oxidative burden.

In yet another embodiment, one of the two active agents is an anti-inflammatory agent that may be a non-steroid anti-inflammatory drug such as, but not limited to, ibuprofen, indomethacin, nimesulide, celecoxib, rofecoxib, valdecoxib, parecoxib, flurbiprofen, sulindac; rofecoxib celecoxib, nabumetone, naproxen, aspirin, ketoprofen, diclofenac, piroxicam, diflunisal, fenoprofen, sulindac, or meclofen; and the protein phycocyanin (Pc); and an anti-inflammatory steroid such as, but not limited to methylprednisolone.

In a preferred embodiment, the pharmaceutical composition of the invention comprises (i) pramipexole in combination with rasagiline, selegiline, ropinirole, piribedil, bromocriptine, pergolide, lisuride, cabergoline, apomorphine, rotigotine, levodopa, levodopa with carbidopa, levodopa with carbidopa and entacapone, levodopa with carbidopa and tolcapone, amantadine, or minocycline;

(ii) ropinirole in combination with rasagiline, selegiline, piribedil, bromocriptine, pergolide, lisuride, cabergoline, apomorphine, rotigotine, levodopa, levodopa with carbidopa, levodopa with carbidopa and entacapone, levodopa with carbidopa and tolcapone, amantadine, or minocycline;

(iii) piribedil in combination with rasagiline, selegiline, bromocriptine, pergolide, lisuride, cabergoline, apomorphine, rotigotine, levodopa, levodopa with carbidopa, levodopa with carbidopa and entacapone, levodopa with carbidopa and tolcapone, amantadine, or minocycline;

(iv) bromocriptine in combination with rasagiline, selegiline, pergolide, lisuride, cabergoline, apomorphine, rotigotine, levodopa, levodopa with carbidopa, levodopa with carbidopa and entacapone, levodopa with carbidopa and tolcapone, amantadine, or minocycline;

(v) pergolide in combination with rasagiline, selegiline, lisuride, cabergoline, apomorphine, rotigotine, levodopa, levodopa with carbidopa, levodopa with carbidopa and entacapone, levodopa with carbidopa and tolcapone, amantadine, or minocycline;

(vi) lisuride in combination with selegiline, rasagiline, cabergoline, apomorphine, rotigotine, levodopa, levodopa with carbidopa, levodopa with carbidopa and entacapone, levodopa with carbidopa and tolcapone, amantadine, or minocycline;

(vii) cabergoline in combination with rasagiline, selegiline, apomorphine, rotigotine, levodopa, levodopa with carbidopa, levodopa with carbidopa and entacapone, levodopa with carbidopa and tolcapone, amantadine, or minocycline;

(viii) apomorphine in combination with selegiline, rasagiline, rotigotine, levodopa, levodopa with carbidopa, levodopa with carbidopa and entacapone, levodopa with carbidopa and tolcapone, amantadine, or minocycline;

(ix) rotigotine in combination with rasagiline, selegiline, levodopa, levodopa with carbidopa, levodopa with carbidopa and entacapone, levodopa with carbidopa and tolcapone, amantadine, or minocycline;

(x) selegiline in combination with levodopa, levodopa with carbidopa, levodopa with carbidopa and entacapone, levodopa with carbidopa and tolcapone, amantadine, minocycline, or rasagiline;

(xi) rasagiline in combination with levodopa, levodopa with carbidopa, levodopa with carbidopa and entacapone, levodopa with carbidopa and tolcapone, amantadine, or minocycline;

(xii) amantadine in combination with levodopa, levodopa with carbidopa, levodopa with carbidopa and entacapone, levodopa with carbidopa and tolcapone, or minocycline; and (xiii) minocycline with levodopa, levodopa with carbidopa, levodopa with carbidopa and entacapone, or levodopa with carbidopa and tolcapone.

It has been found in accordance with the present invention that combinations of pramipexole with rasagiline or selegiline, or ropinirole with rasagiline or selegiline, are more efficient in improving or maintaining the viability of MPP+ or serum-starved neuronal cells in vitro than are the same compounds when used separately (see Example 1). It has further been found in accordance with the present invention that a combination of pramipexole with rasagiline is much more efficient in restoring locomotion activity and dopamine level in dopamine neurons in the substantia nigra in MPTP treated mice than is either of the two compounds when administered alone (see Example 2). This is true both for mice treated for 5 days and for mice treated for 11 days. According to these findings the combination therapy confer neuroprotective activity and as a result attenuation of damage and normal sensitivity of the dopaminergic system to dopamine agonists. The combination therapy also seems to restore or balance the potentially unbalanced response of the animal to the "augmenting dopaminergic therapy" conferred by a dopamine agonist when administered alone.

Thus, in preferred embodiments, the pharmaceutical composition comprises a combination of a dopamine receptor agonist in combination with a MAO inhibitor. For example, the pharmaceutical composition comprises a dopamine receptor agonist selected from pramipexole, ropinirole piribedil, lisuride, cabergoline, apomorphine, rotigotine, bromocriptine or pergolide in combination with a propargylamine type MAO-B inhibitor such as rasagiline or selegiline. In particular, the pharmaceutical composition comprises (i) pramipexole in combination with rasagiline; (ii) pramipexole in combination with selegiline; (iii) ropinirole in combination with rasagiline; or (iv) ropinirole in combination with selegiline.

The molar ratio of pramipexole to rasagiline is selected from 1:1 2:1, 3:1, 4:1, 5:1, 6:1, 7:1, 8:1, 9:1, 10:1, 12:1, 14:1, 16:1, 18:1, 20:1, 30:1, 40:1, 50:1 or 100:1; the molar ratio of pramipexole to selegiline is selected from 1:1 2:1, 3:1, 4:1, 5:1, 6:1, 7:1, 8:1, 9:1, 10:1, 12:1, 14:1, 16:1, 18:1, 20:1, 30:1, 40:1, 50:1 or 100:1; the molar ratio of ropinirole to selegiline is selected from 1:1 2:1, 3:1, 4:1, 5:1, 6:1, 7:1, 8:1, 9:1, 10:1, 12:1, 14:1, 16:1, 18:1, 20:1, 30:1, 40:1, 50:1 or 100:1; said molar ratio of ropinirole to rasagiline is selected from 1:1 2:1, 3:1, 4:1, 5:1, 6:1, 7:1, 8:1, 9:1, 10:1, 12:1, 14:1, 16:1, 18:1, 20:1, 30:1, 40:1, 50:1 or 100:1.

In a most preferred embodiment, the molar ratio of pramipexole to rasagiline is between about 1:1 and about 10:1. The fixed dose combination having said molar ratio may be from about 0.01 mg to about 45 mg, preferably from about 0.1 mg to about 6 mg, of pramipexole, and from about 0.01 mg to about 10 mg, preferably from about 0.05 mg to about 1 mg, of rasagiline. Since the molecular weights of the two compounds are very close, the molar ratio and the weight:weight ratio are similar and the two types of ratios are related to interchangeably in the present application.

The pharmaceutical composition of the invention contains a fixed dose combination of the two active agents in which each of the active agents is formulated for immediate release, controlled release, or both immediate and controlled release.

In preferred embodiments, the pharmaceutical composition comprises a fixed dose combination selected from: (i) controlled release pramipexole and controlled release rasagiline or selegiline; (ii) controlled release pramipexole and immediate release rasagiline or selegiline; (iii) controlled and immediate release pramipexole and controlled and immediate release rasagiline or selegiline, wherein up to 50% of pramipexole and of rasagiline or selegiline is in the controlled release form; (iv) controlled release ropinirole and controlled release rasagiline or selegiline; (v) controlled release ropinirole and immediate release rasagiline or selegiline; and (vi) controlled release apomorphine and controlled release combination of levodopa and carbidopa.

In the case of controlled release formulation, the dose of pramipexole may be from about 0.01 mg to about 45 mg and the dose of rasagiline may be from about 0.01 mg to about 10 mg, i.e. the dose of pramipexole may be 0.01, 0.02, 0.04, 0.06, 0.08, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, 10, 12, 14, 16, 18, 20, 25, 30, 35, 40 or 45 mg, while the dose of rasagiline may be 0.01, 0.02, 0.04, 0.06, 0.08, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9 or 10 mg, with a molar ratio as defined above. In particular, the doses of pramipexole and rasagiline in the fixed dose combination may be, but is not limited to, 6 mg pramipexole and 0.6 mg rasagiline; 4.5 mg pramipexole and 1.2 mg rasagiline; 3 mg pramipexole and 0.3 mg rasagiline; 3 mg pramipexole and 1.2 mg rasagiline; 2 mg pramipexole and 0.2 mg rasagiline; or 1.5 mg pramipexole and 1.2 mg rasagiline.

The pharmaceutical composition of the invention may be in any suitable form, for example tablets such as matrix tablets, in which the release of a soluble active is controlled by having the active diffuse through a gel formed after the swelling of a hydrophilic polymer brought into contact with dissolving liquid (in vitro) or gastro-intestinal fluid (in vivo). Many polymers have been described as capable of forming such gel, for example derivatives of cellulose, in particular the cellulose ethers such as hydroxypropyl cellulose, hydroxymethyl cellulose, methyl cellulose or methyl hydroxypropyl cellulose, and among the different commercial grades of these ethers are those showing fairly high viscosities. Also bilayer tablets are contemplated; these tablets are made up of two or more distinct layers of granulation compressed together with the individual layers lying one on top of another, with each separate layer containing a different active. Bilayer tablets have the appearance of a sandwich because the edge of each layer or zone is exposed.

The pharmaceutical composition may also comprise microencapsulated active ingredient, in which small droplets of the active is surrounded by a coating or a membrane to form particles in the range of a few micrometers to a few millimeters.

In some embodiments, the invention provides pharmaceutical compositions for oral administration which are solid and may be in the form of granulate, granules, grains, beads or pellets, which are mixed and filled into capsules or sachets or are compressed to tablets by conventional methods. In some preferred embodiment, there is provided a tablet in which the two agents are present in at least two separate layers, i.e. a bi-layer or multilayer tablet, in which the layers comprising the first and second agents may be separated by an intermediate, inactive layer, for example a layer comprising one or more disintegrants.

Another contemplated formulation is depot systems, based on biodegradable polymers. As the polymer degrades, the active ingredient is slowly released. The most common class of biodegradable polymers is the hydrolytically labile polyesters prepared from lactic acid, glycolic acid, or combinations of these two molecules. Polymers prepared from these individual monomers include poly(D,L-lactide) (PLA), poly(glycolide) (PGA), and the copolymer poly(D,L-lactide-co-glycolide) (PLG).

Useful dosage forms of the pharmaceutical compositions include orally disintegrating systems including, but not limited to solid, semi-solid and liquid systems including disintegrating or dissolving tablets, soft or hard capsules, gels, fast dispersing dosage forms, controlled dispersing dosage forms, caplets, films, wafers, ovules, granules, buccal/mucoadhesive patches, powders, freeze dried (lyophilized) wafers, chewable tablets which disintegrate with saliva in the buccal/mouth cavity and combinations thereof. Useful films include, but are not limited to, single layer stand alone films and dry multiple layer stand alone films.

Another useful dosage form is a long lasting injectable system, such as a liposomal gel consisting of e.g. poloxamer 407 and a liposomal solution containing the actives.

The two active agents in the composition may also be formulated in a pellets dosage form (capsules) with different release patterns: one agent for immediate release and the other for controlled release, or each of the agents both for immediate and controlled release, in which case 10, 20, 30, 40, 50, 60, 70, 80 or 90% of the dose is for controlled release and the remaining for immediate release.

The pharmaceutical composition of the invention comprises one or more pharmaceutically acceptable excipients. For example, a tablet may comprise at least one filler, e.g., lactose, ethylcellulose, microcrystalline cellulose, silicified microcrystalline cellulose; at least one disintegrant, e.g. cross-linked polyvinylpyrrolidinone; at least one binder, e.g. polyvinylpyridone, hydroxypropylmethyl cellulose; at least one surfactant, e.g. sodium laurylsulfate; at least one glidant, e.g. colloidal silicon dioxide; and at least one lubricant, e.g. magnesium stearate.

The present invention also provides a method for treatment of Parkinson's disease, which comprises administering to a patient in need a pharmaceutical composition of the invention as described herein.

The invention further relates to the use of two active agents selected from compounds having either neuroprotective or symptomatic effects, or both, in Parkinson's disease patients, for the preparation of a pharmaceutical composition for the treatment of Parkinson's disease.

The following models of Parkinson's disease are known in the art and may be used according to the present invention. Free radical damage is strongly implicated as a mediator of dopaminergic neuronal death in Parkinson's disease. Oxidative stress associated with aging, mitochondrial dysfunction, protein aggregation, dopamine oxidation and iron overload is thought to contribute to the pathogenesis of Parkinson's disease.

A significant body of biochemical data from human brain autopsy studies and those from animal models point to an ongoing process of oxidative stress in the substantia nigra which could initiate dopaminergic neurodegeneration. It is not known whether oxidative stress is a primary or secondary event. Nevertheless, oxidative stress, as induced by neurotoxins 6-hydroxydopamine (6-OHDA) and MPTP (N-methyl-4-phenyl-1,2,3,6-tetrahydropyridine), has been used in animal models to investigate the process of neurodegeneration with the intent to develop antioxidant neuroprotective drugs.

The neurotoxin MPTP is converted in the brain into the positively charged molecule MPP+ (1-methyl-4-phenylpyridinium) by the enzyme MAO-B, causing parkinsonism in primates by killing certain dopamine-producing neurons in the substantia nigra. It acts by interfering with oxidative phosphorylation in mitochondria, causing depletion of ATP and cell death. It also inhibits the synthesis of catecholamines, reduces levels of dopamine and cardiac norepinephrine, and inactivates tyrosine hydroxylase.

Early studies with 6-OHDA indicated that this neurotoxin is a highly reactive substance, which is readily autoxidised and oxidatively deaminated by monoamine oxidase to give rise to hydrogen peroxide and reactive oxygen species (ROS). It was inferred that this neurotoxin exerts its neurodegenerative action via oxidative stress. The consequence of oxidative stress is the initiation of ROS generation, followed by brain membrane lipid peroxidation. The possibility that an endogenous toxin, similar to a neurotoxin such as 6-OHDA, may be formed in the brain and involved in the process of the neurodegeneration has been envisaged on many occasions.

Mitochondrial dysfunction has been linked to Parkinson's disease. Specifically, there are systemic reductions in the activity of complex I of the mitochondrial electron transfer chain in brain, muscle, and platelets of Parkinson's disease patients.

Rotenone, a common pesticide, is a high-affinity inhibitor of complex I of the mitochondrial electron transfer chain. The rotenone model of Parkinson's disease has been substantiated by involvement of pesticide exposure and systemic complex I dysfunction in Parkinson's disease etiology. Although rotenone causes uniform complex I inhibition throughout the brain, rotenone-treated rats demonstrated many characteristics of Parkinson's disease, including selective nigrostriatal dopaminergic degeneration, formation of ubiquitin and-synuclein-positive nigral inclusions, and motor deficits. Although the rotenone model demonstrated the potential relevance of complex I defects to Parkinson's disease pathogenesis, the mechanisms through which systemic complex I dysfunction produce neurotoxicity are not known.

The invention will now be illustrated by the following non-limiting examples.

EXAMPLES

Materials (i) Cells:

PC-12 pheochromocytoma rat adrenal medulla cells (ATCC Number: CRL-1721) and human bone marrow neuroblastoma SK-N-SH cells (ATCC Number: HTB-11), obtained from ATCC, are used in the experiments described below. PC12 cells were maintained in F12K medium (Gibco) containing 15% horse serum, 2.5% Bovine serum, glutamine and antibiotics. SK-N-SH cells were grown in Eagle's minimum essential medium (Biological industries) containing 10% bovine serum, glutamine and antibiotics. Both cell lines were maintained at 37° C. and 5% CO2

Methods.

In Vitro Neuroprotection Assay.

For neuroprotection experiment cells were plated (1 or $0.5 \times 10^5$ Cells per well) on poly-L-lysine (Sigma) coated 96 wells tissue culture plates. Twenty four hours after plating the medium was exchanged with fresh growth medium with or without the tested drugs in the absence or presence of stressor. Cell cytotoxicity was induced by either serum starvation or Methyl-4-phenylpyridium (MPP+), 250 uM and 125 uM for PC12 and SK cells respectively. Drugs were added in different concentration alone and in combination, 30 minutes prior to the insult for a subsequent 48 or 72 hours. Neuronal cell injury was evaluated by a colorimetric assay for mitochondrial function using the MTT test (Sigma). The MTT test is based on the conversion of MTT to blue formasan crystals by viable cells. 5 mg/ml MTT reagent was added to each well (1:10 final dilution in each well). Cells were incubated for 1 hour at 37° C. and 5% CO2. Excess MIT was removed, and remaining formasan crystals were dissolved in 50 ul DMSO and were quantified in Elisa reader. The wavelength of the measurement of formasan product was 550 nm and the reference wavelength was 620 nm.

Sample Preparation for HPLC Analysis of DA and Metabolites.

Striatum tissue samples were homogenized in ice in 500 ul homogenization buffer (0.1M perchloric acid, 0.02% EDTA and 1% ETOH) using OMNI Tip homogenizing kit of OMNI International (intermediate speed, 3×10 seconds with 5 seconds intervals). The homogenates were sonicated for 5 minutes then centrifuged at 15,000 RPM at 4° C. for 15 min. The supernatants were transferred into fresh tubes and Dopamine content was analyzed by HPLC.

Example 1

In Vitro Rapid Screening of Drug Combinations Protecting from Cell Death

Two in vitro systems were used to assess the effect of drug combinations on stressed cells, in which 4 drug combinations were used on each one of the stressors. The ratio of the 2 drugs was optimized by trying varying ratios: (1:4 and 1:10) and time dependent exposure. The drug combinations tested are (a) pramipexole in combination with rasagiline; (b) pramipexole in combination with selegiline; (c) rasagiline in combination with ropinirole; and (d) selegiline in combination with ropinirole.

1.1. Neuroprotection.

The goal of the present experiment is to characterize the ability of the drug combinations to protect from cell death in vitro.

(a) PC12 and SK-N-SH Cells were incubated with 3 different concentrations of MPP+ (125, 250, and 500 µM) or in growth medium lacking serum for 48 and 72 hours.

(b) Various drug combinations at various drug ratios as stated above were tested. The concentrations used were as follows: ropinirole, 400 µM, 200 µM, 100 µM, 50 µM; rasagiline, 400 µM, 200 µM, 100 µM, 50 µM, 10 µM; pramipexole, 400 µM, 200 µM, 100 µM, 50 µM; selegiline, 100, 50 µM, 10 µM, 1. Cell protection was detected by MTT.

(c) The experiment is repeated 3 times to demonstrate reproducibility.

Figure 1A:
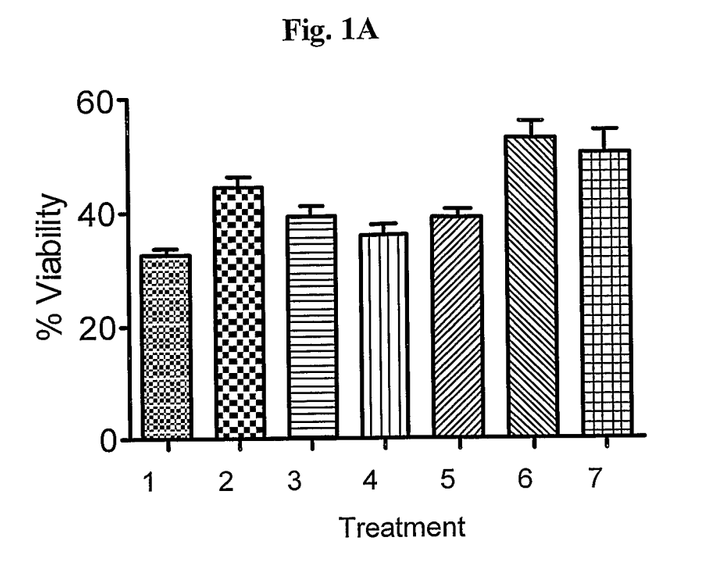
Figure 1B:
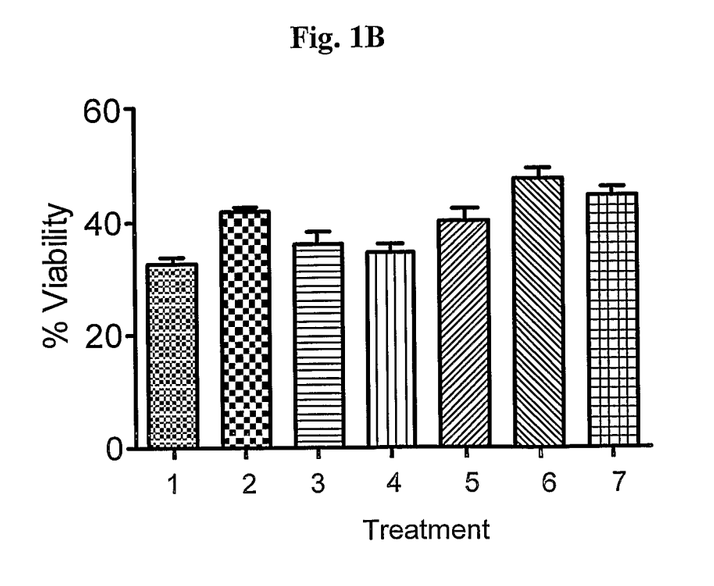
Figure 1C:
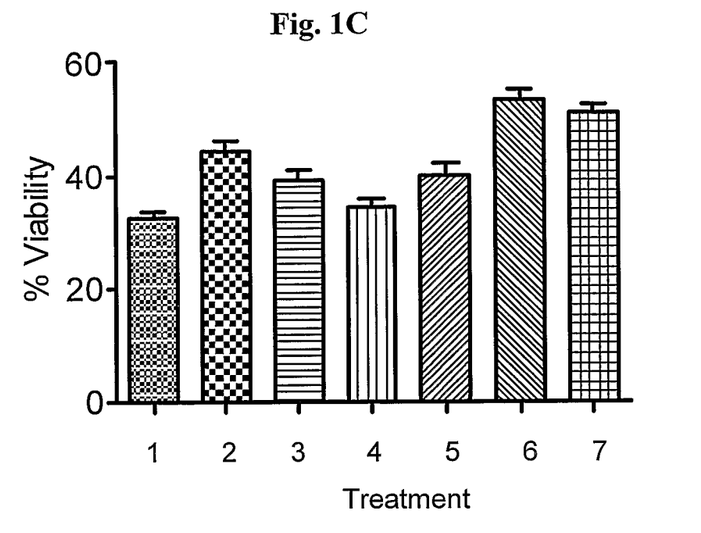
Figure 2A:
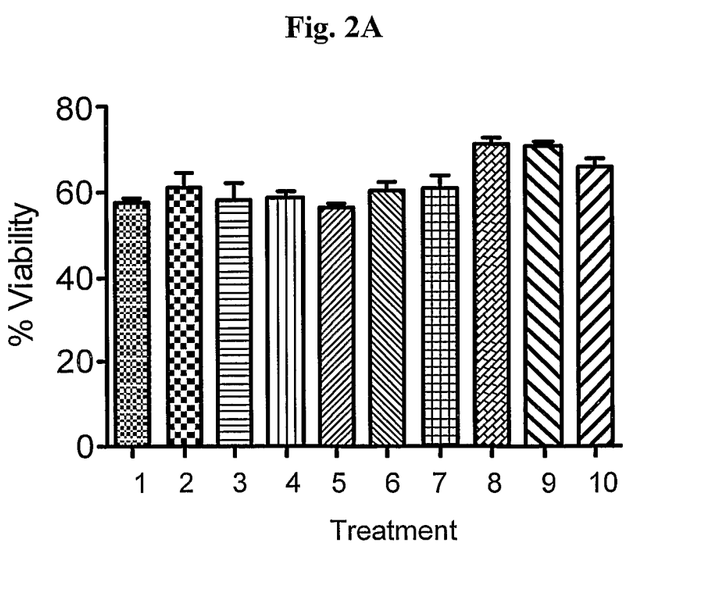
Figure 2B:
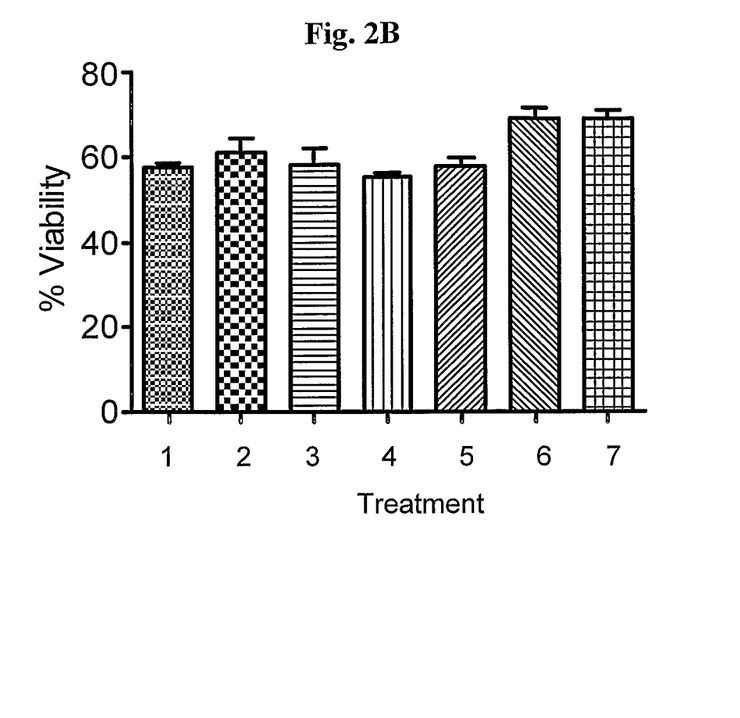
Figure 2C:
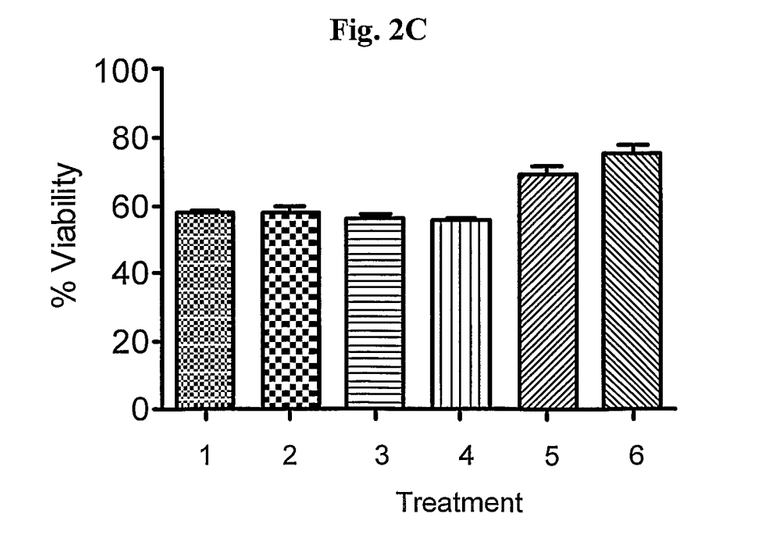
Figure 2D:
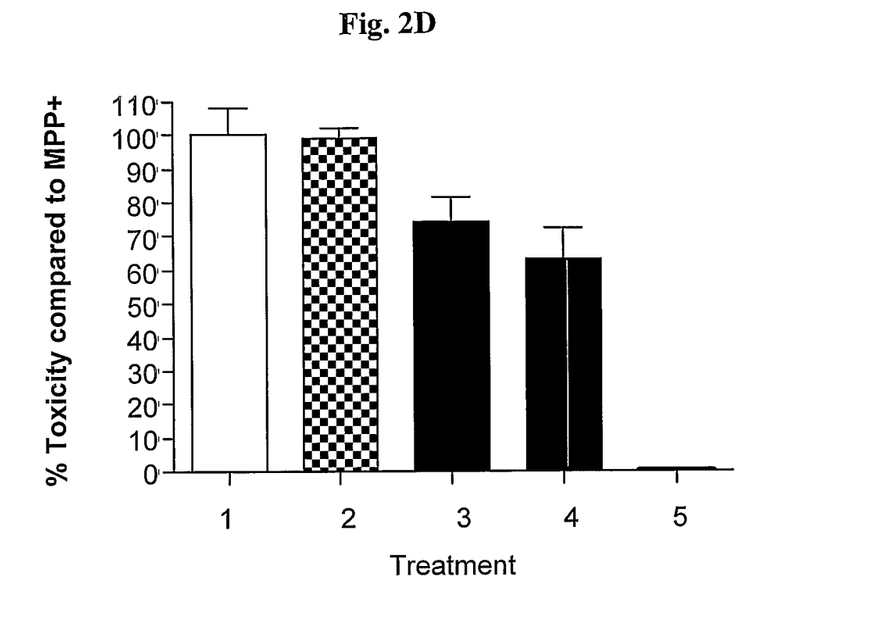

We have presented here two in vitro models for studying neuroprotection: serum starved (FIGS. 1A-C) and MPP+ treated cells FIGS. 2A-D), both strategies induced apoptosis in PC12 cells. When cells treated in parallel with an apoptosis inducer and one parkinson drug alone, either Ropinirole (FIG. 1A, 1C, 2A, 2B), Rasagiline (FIG. 1A, 2A, 2C), Pramipexole (FIG. 1B, 2C) or Selegiline (FIG. 1B, 1C, 2B, 2C), the effect on neuroprotection was minor. Cell survival was increased and neuroprotection effect was pronounced when two drugs were applied together, one drug from the DRA family and the other from the MAO inhibitor family (FIGS. 1-C and FIGS. 2A-C). The combinations used to treat serum-free medium induced apoptosis were ropinirole, 200 µM:rasagiline, 50 µM; ropinirole, 100 µM:rasagiline, 10 µM (FIG. 1A); pramipexole, 200 µM:selegiline, 50 µM; pramipexole, 100 µM:selegiline, 10 µM (FIG. 1B); ropinirole, 200 µM:selegiline, 50 µM; and ropinirole, 100 µM:selegiline, 10 µM (FIG. 1C). The combinations used to treat MPP+ induced apoptosis were ropinirole, 400 µM:rasagiline, 100 µM; ropinirole, 200 µM:rasagiline, 50 µM; ropinirole, 100 µM:rasagiline, 10 µM (FIG. 2A); ropinirole, 400 µM:selegiline, 100 µM; ropinirole, 200 µM:selegiline, 50 µM (FIG. 2B); pramipexole, 400 µM:rasagiline, 100 µM; pramipexole, 400 µM:selegiline, 100 µM (FIG. 2C); and pramipexole, 200 µM:rasagiline, 200 µM (FIG. 2D). These data show the advantage of combination treatment.

Example 2

In Vivo Characterization of Drug Combinations in Models of Parkinson's Disease

The tested drugs were administered to the mice (10 mice per group) at two different dosages 30 minutes prior to MPTP administration (daily for 5 days). Saline-injected mice are used as control (naïve mice). Mice were treated according to the following plan:

TABLE 1

Treatment of MPTP induced mice with single or combination Parkinson drugs.

| Group | Treatment |
|---|---|
| 1 | Naive mice |
| 2 | MPTP |
| 3 | MPTP + Rasagiline, 0.05 mg/Kg |
| 4 | MPTP + Rasagiline, 0.1 mg/Kg |
| 5 | MPTP + Pramipexole, 0.5 mg/Kg |
| 6 | MPTP + Pramipexole, 1 mg/Kg |
| 7 | MPTP + Combination of 3 and 5 |
| 8 | MPTP + Combination of 4 and 6 |

The effect of the treatment was assessed by behavioral tests on days 5 and 11 (Rota rod, and open field) and by measurement of dopamine/dihydroxyphenylacetic acid and Homovanillic acid striatal content on day 15.

2.1 Beneficial Effect of the Combination on Locomotion Activity.

Figure 3A:
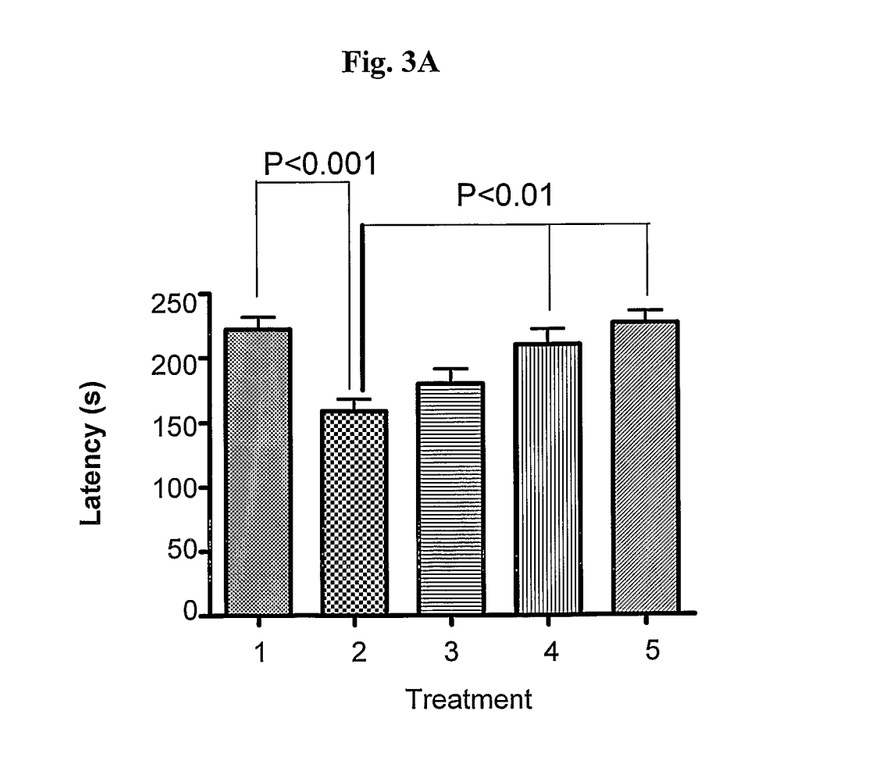
FIGS. 3A-C show the beneficial effect of a drug combination on locomotion activity in MPTP treated mice as measured by Rota-rod latency (3A) or Rota-rod distance (3B-C) on day 5 (3A-B) and on day 11 (3C) of the study. (1) control; (2) MPTP; (3) Rasagiline-0.1 mg/Kg; (4) Pramipexole, 1 mg/Kg; (5) combination of (3) and (4).
Figure 3B:
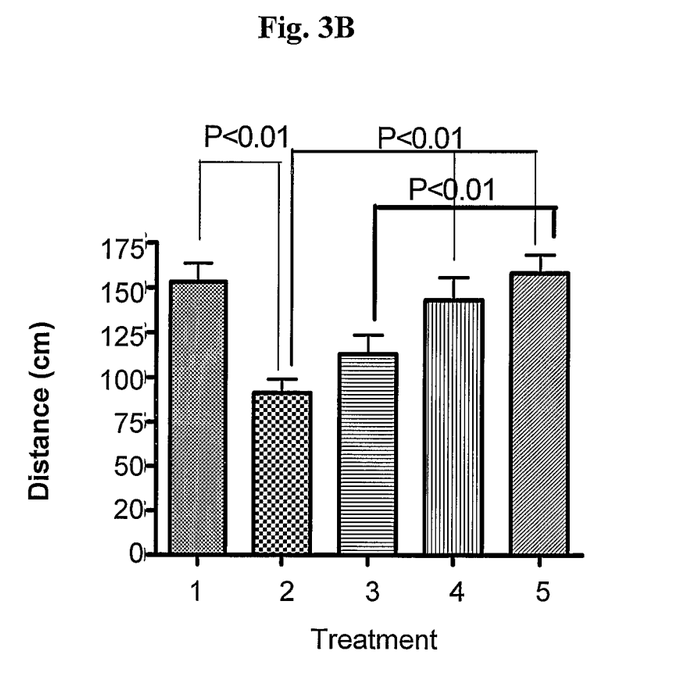

FIGS. 3A-B show the locomotion activity as tested by Rota rod latency (FIG. 3A) and Rota rod distance (FIG. 3B) on day 5 of the study (5 drug administrations).

It can be seen that MPTP causes about 30% decrease in locomotion activity, which is restored by both drugs alone and by the combination. The differences in locomotion activity are harder to detect than the difference in biochemical marker levels such as the dopamine levels; however, it is clearly seen that the trend of significant beneficial differences are observed with combination treatment also in the behavioral tests, related to and in agreement with the dopamine level effects (see below).

It should be noted that in general, behavioral effects in humans are detected at the point where dopamine levels are decreased by almost 80%-90%. Thus, it is very difficult to quantitate these effects and the fact that significant differences are observed, is very encouraging regarding the beneficial effect of the treatment.

Figure 3C:
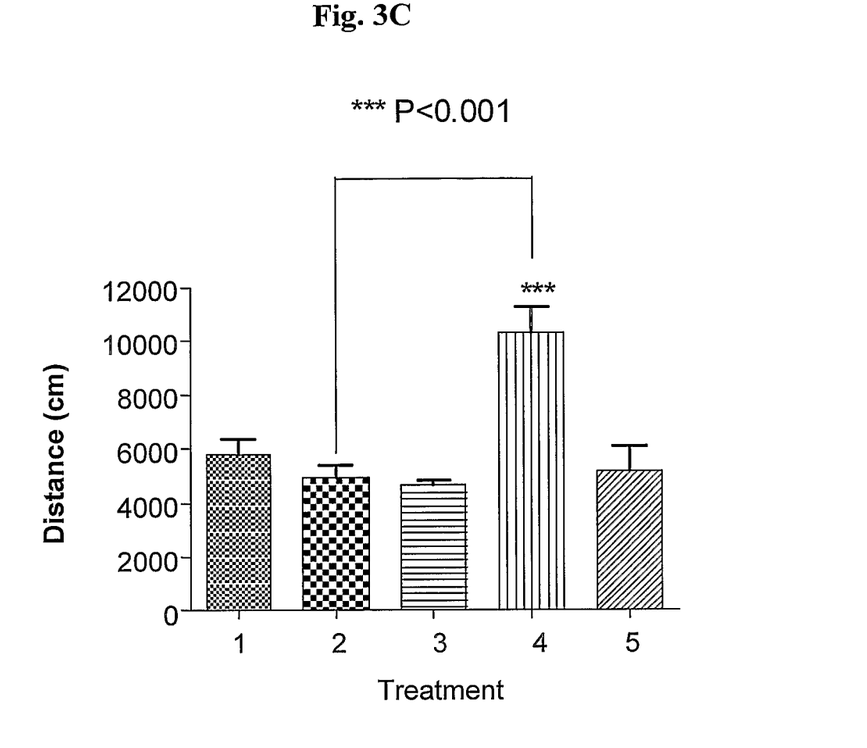

FIG. 3C describes the locomotion activity, as represented by open-field test, on day 11 of the study. Day 11 represents longer treatment relative to the measurements on day 5, and can be considered semi-chronic. Chronic treatment with dopamine agonist often caused significant increase in locomotion activity. This over-activity is the predicted response to dopamine agonist in chronically depleted models.

Similar behavior is revealed on day 11 of our study, in the open field test. The locomotion activity is almost twice higher than control, non MPTP treated level.

Following combination administration, over-activity was completely abolished suggesting: (1) Neuroprotective activity of the combination and as a result attenuation of damage and normal sensitivity of the dopaminergic system to dopamine agonists; (2) Potential restoration/balancing of response to "augmenting dopaminergic therapy". Diminishing potential unbalanced activity of dopamine agonist when administered alone.

It should be noted that at day 11, MPTP treatment has been ceased for over 6 days, which can explain the smaller differences between MPTP treated and normal animals, an expected phenomenon in this model. However, the attenuation of dopamine agonist effect is still very significant, implying that combining the effects observed on day 5, namely the restoration of locomotion activity to normal when each drug alone fails to do so, and the observation on day 11, namely attenuation of possible side effects, suggest highly beneficial potential of the combination treatment, from both efficacy and safety point of view.

2.2 Beneficial Effect of the Combination on Brain Dopamine Levels.

Figure 4:
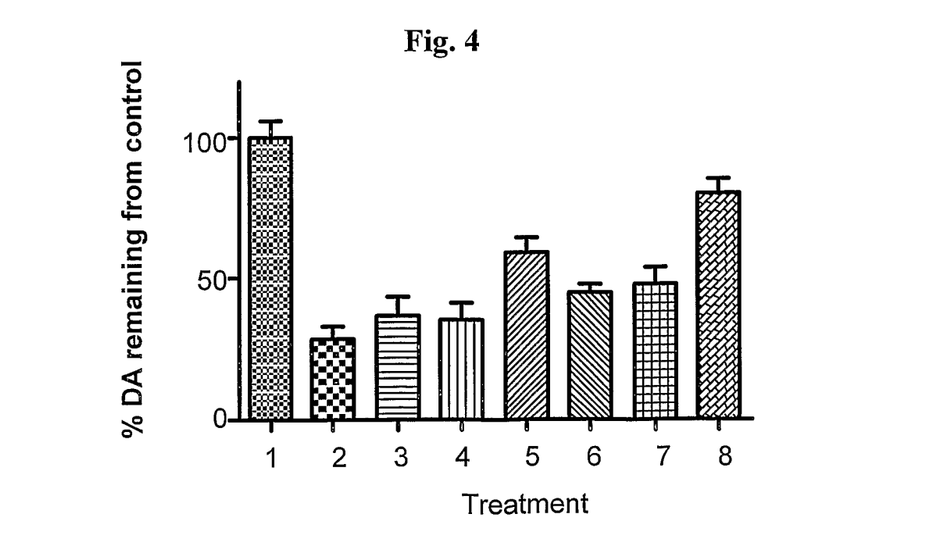
FIG. 4 shows the beneficial effect of a drug combination on dopamine levels in MPTP treated mice (1) Naive mice; (2) MPTP; (3) Rasagiline 0.05 mg/Kg; (4) Pramipexole 0.5 mg/Kg; (5) Combination of (3) and (4); (6) Rasagiline 0.1 mg/Kg; (7) Pramipexole 1 mg/Kg; (8) Combination of (6) and (7). DA, dopamine.

As can be seen in FIG. 4, MPTP treatment (column 2) caused over 70% depletion in dopamine levels relative to naïve mice (column 1). Treatment with the low doses of both rasagiline and pramipexole alone (0.05 mg/kg and 0.5 mg/kg, respectively), did not cause a significant restoration of dopamine levels (columns 3, 4), while the combination of the two low doses, led to a significant increase in dopamine levels (column 5). Similarly, the high doses of each component alone (0.1 mg/kg rasagiline and 1 mg/kg pramipexole), (columns 6, 7) caused a significant but small increase, while the combination led to dopamine level restoration to 80% of the normal level (column 8).

It is important to note, that doubling the dose of each drug alone (columns 3 vs. 5 and 4 vs. 6) caused very small increase in the effect, however adding the other drug caused a remarkable difference, implying that the increase originated from the two different mechanisms of the drugs.

It should further be noted that in order to restore dopamine levels in MPTP challenged mice in our experimental model, by administering rasagiline alone, a dose of at least 0.5 mg/kg is required, while pramipexole alone should be administered at a dose higher than 1 mg/kg (not shown). Thus, the combination of the two compounds enables a very significant reduction of their doses. This is extremely important since it reduces unwanted side-effects and permits the effective use of the drugs during a longer period.

Example 3

Design of Fixed Dose Combination Formulation

The formulation for the Fixed Dose Combination (FDC) is designed to provide optimal release profile that maximize the combination effect. Specifically for the combination of rasagiline-pramipexole as an example, the pharmacokinetics and half-lives of the two components are very different. While rasagiline is given once daily, pramipexole is administered up to 4 times per day due to its pharmacokinetic (PK) and pharmacodynamic (PD) properties. Thus, in order to maximize the combination effect, the formulation is designed with two release profiles, that cause the components to be distributed and absorbed in an optimal rate for their combination effect. One possibility is that rasagiline is formulated for immediate release and pramipexole with sustained release. The other option is two sustained release profiles optimized for each of the components.

The invention claimed is:

1. A method for treatment of Parkinson's disease, comprising administering to a patient in need thereof a daily dose of a pharmaceutical composition comprising a pharmaceutically acceptable carrier and a fixed dose combination of controlled release pramipexole and controlled release rasagiline, wherein said fixed dose combination contains from about 0.01 mg to about 1.5 mg of pramipexole and from about 0.01 mg to about 1 mg of rasagiline.

2. The method according to claim 1, wherein said fixed dose combination is in the form of a tablet, a capsule, a sachet, an orally disintegrating film, wafers, or a long lasting injectable system.

3. The method according to claim 1, wherein said fixed dose combination contains 0.01 to 1.4 mg pramipexole.

4. The method according to claim 1, wherein said fixed dose combination contains 0.01 to 0.9 mg rasagiline.

5. The method according to claim 4, wherein said fixed dose combination contains 0.01 to 1.4 mg pramipexole.

* * * * *